US006221664B1

(12) United States Patent
Wen et al.

(10) Patent No.: US 6,221,664 B1
(45) Date of Patent: Apr. 24, 2001

(54) COMPOSITE VACCINE WHICH CONTAINS ANTIGEN, ANTIBODY AND RECOMBINANT DNA AND ITS PREPARING METHOD

(75) Inventors: Yumei Wen; Lifang He; Di Qu, all of Shanghai (CN)

(73) Assignee: Shanghai Medical University, Shanghai (CN)

(*) Notice: Subject to any disclaimer, the term of this patent is extended or adjusted under 35 U.S.C. 154(b) by 0 days.

(21) Appl. No.: 09/171,704

(22) PCT Filed: Feb. 23, 1998

(86) PCT No.: PCT/CN98/00025

§ 371 Date: Dec. 22, 1998

§ 102(e) Date: Dec. 22, 1998

(87) PCT Pub. No.: WO98/37912

PCT Pub. Date: Sep. 3, 1998

(30) Foreign Application Priority Data

Feb. 26, 1997 (CN) .................................................. 97106291

(51) Int. Cl.$^7$ ........................... C12N 15/00; C12N 15/09; A61K 39/29; A61K 39/295

(52) U.S. Cl. ................... 435/440; 435/320.1; 424/189.1; 424/202.1; 424/227.1; 424/228.1

(58) Field of Search ........................ 425/189.1; 435/69.1, 435/320.1, 440; 514/44; 424/130.1, 139.1, 149.1, 180.1, 193.1, 196.11, 225.1, 227.1, 134.1, 136.1, 161.1, 184.1, 189.1, 202.1, 228.1

(56) References Cited

FOREIGN PATENT DOCUMENTS

| 1093927 | 10/1994 | (CN) . |
| PCT/FR94/ 00483 | 4/1994 | (WO) . |
| PCT/US95/ 00997 | 1/1995 | (WO) . |

OTHER PUBLICATIONS

Mancini et al; DNA—mediated immunization in a transgenic mouse model of the hepatitsi B surface antigen chronic carrier state. Proc. Natl. Acad. Sci. USA, vol. 93, Oct. 1996, pp. 12496–12501.
Wen et al., Hepatitis B Vaccine anti–HBs complex as approach for vaccine therapy, The Lancet, vol. 345, Jun. 17, 1995, pp. 1575–1576.
McDonnell et al., Molecular Medicine DNA Vaccines, The New England Journal of Medicine, vol. 334, No. 1, Jan. 4, 1996, pp. 42–45.
Michel et al., DNA—mediated immunization to the hepatitis B surface antigen in mice: Aspects of the humoral response mimic hepatitis B viral infection in humans, Pro. Natl. Acad. Sci. USA, vol. 92, Jun. 1995, pp. 5307–5311.
Tse Wen Chang, Regulation of immune response by antibodies: the importance of antibody and monocyte Fc receptor interaction in T–cell activation, Immunology Today, vol. 6, No. 8, 1985, p. 245–249.
Davis et al., DNA—based immunization induces continuous secretion of hepatitis B surface antigen and high levels of circulating antibody, Human Molecular Genetics, Oxford University Press, 1993, vol. 2, No. 11 pp. 1847–1851.
Houston et al., Inactivated Venezuelan Equine Encephalomylitis Virus Vaccine Complexed with Specific Antibody: Enhanced Primary Immune Response and Altered Pattern of Antibody Class Elicited, The Journal of Infectious Diseases, vol. 135, No. 4, Apr. 1977, pp. 600–610.
Stoner et al., Enhanced Antitoxin Responses in Irradiated Mice Elicited by Complexes of Tetanus Toxoid and Specific Antibody, J. immunol., vol. 91, 1963, pp. 761–770.
Randall et al., Immunization against Multiple Viruses by Using Solid–Matrix–Antibody–Antigen Complexes, Journal of Virology, Apr. 1989, vol. 63, No. 4, pp. 1808–1810.
McDonell et al. New England Journal of Medicine. 334(1): 42–45, Jan. 1996.*
Michel et al. Pro. Nat'l Academy of Sciences USA. 92: 5307–5311, Jun. 1995.*
Wen et al. Lancet. 345: 1575, Jun. 1995.*
Ledley FD. Pharmaceutical Research. 13: 1595–1613, Nov. 1996.*
Barnett et al. J of Neuroimmunology. 64: 163–173, Feb. 1996.*
Robinson HL. Vaccine. 15(8): 785–787. Jun. 1997.*
Wild et al. Vaccine. 16(4): 353–360, Feb. 1998.*
Honorati et al. Gasteroenterology. 112(6): 2017–27. Jun. 1997.*

\* cited by examiner

Primary Examiner—John L. LeGuyader
Assistant Examiner—Carrie Stroup
(74) Attorney, Agent, or Firm—Merchant & Gould P.C.

(57) ABSTRACT

This invention is a vaccine prepared from antigen-antibody-recombinant plasmid DNA complex.

This invention is a complex vaccine composed of at least one microbial source antigen and its (their) specific antibody or specific immunoglobulin complexed with one or more recombinant DNA(s) from the gene or genes of microbes. Immunization with this complex vaccine induces enhanced specific humoral and cellular immune responses in infected individuals with immune tolerance or immune defects against specific microbial infections. The advantages of this complex vaccine are: antigen presentation via various modes; more rapid induction of immune responses; less amount of components required to induce immune responses; increased stability of the vaccine; and can be applied by injection, intranasal or other routes of topical immunization. Experiments showed that the titer, percentage of antibody sero-conversion and specific cell-mediated immune responses in mice immunized with this complex vaccine were higher than those in control groups.

This invention also includes the method for preparation of this complex vaccine.

11 Claims, No Drawings

COMPOSITE VACCINE WHICH CONTAINS ANTIGEN, ANTIBODY AND RECOMBINANT DNA AND ITS PREPARING METHOD

FIELD OF THE INVENTION

This invention relates to vaccines, and/or immunogenic composition methods for their preparation and uses therefore. More particularly, the present invention comprises a method of preparing complex vaccines and/or immunogenic composition composed of antigen-antibody and recombinant DNA(s), especially microbial source antigen(s) and its(their) antibody and recombinant DNA(s) as immunogen (s) or adjuvant(s), which can be used for prevention or treatment against infectious diseases.

BACKGROUND OF THE INVENTION

Vaccines have been used to prevent infectious diseases, and the successful global elimination of smallpox was attained only through vaccination. However, not all preventive vaccines are as effective as vaccinia; therefore developing measures to improve the quality of vaccines, as well as decreasing the number of inoculations of vaccines to be given are necessary. Aside from preventive vaccines, therapeutic vaccines used for active immunization of patients with chronic bacterial or viral diseases (Tuberculosis, Herpes simplex, Viral hepatitis B, AIDS etc.) have also been developed. There are two categories of therapeutic vaccines, namely specific and non-specific therapeutic vaccines. Immunization with non-specific therapeutic vaccines (e.g. BCG, *Corynebacterium parvum* etc.) can induce non-specific host immune responses, especially cell-mediated immune responses, which showed some effects, but were usually not potent enough to terminate chronic infections. Since specific therapeutic vaccines can induce specific humoral and cellular immune responses in infected hosts, therefore specific therapeutic vaccines are more preferable. Presently, specific therapeutic vaccines can be grouped as: (1). Inactivated or killed whole microbial vaccines. Usually specific strains of microbes were selected and were inactivated or killed for preparation. (2). Recombinant vaccines expressing specific microbial antigen(s). Recombinant technologies were employed to express one or more microbial antigen(s). (3). Chimeric vaccines: Chimeric genes constructed with genes coding for specific microbial antigens fused with genes coding for cytokines (interferons or interleukin-2 etc.) were expressed as fusion proteins and used for active immunization. (4). Synthetic peptide vaccines: Epitopes from microbes were selected and were either used for preparation of synthetic peptides or used for preparation of chimeric peptides (with adjuvants or cytokines added) for active vaccination. (5). Microbial antigen-antibody complex: Appropriate ratio of microbial antigen and antibody complex was used to generate more potent immune responses. (6). Nucleic acid (DNA or polynucleotide, or recombinant DNA vaccine) vaccines: Fragments of genes coding for the protective antigens of microbes were cloned into expression vectors and these recombinant-vector nucleic acid vaccines were used for immunization. Significant enhanced humoral, and especially cellular immune response could be generated by this approach of immunization. Appropriate method of recombinant DNA vaccine delivery into tissues (muscles, skin) is critical, in order to induce effective immune responses. In addition, minimizing the amount of nucleic acid used for induction of effective immune responses is desirable.

Davis H L et al. (*Human Molecular Genetics* 1993;2:1857) demonstrated that by using a vector DNA which contains the encoding gene fragment of hepatitis B surface antigen for DNA-based immunization in mice, secretion of hepatitis B surface antigen and high levels of circulating antibody was detected. A number of publications appeared in the past few years in regard to various microbial nucleic acid (or DNA) vaccination. Among these, Macini M et al (*Proc. Natl. Acad. Sci. USA* 1996; 93:12496) reported by DNA-based immunization in a transgenic mouse model of the hepatitis B surface antigen chronic carrier state, resulted in complete clearance of circulating HBsAg, which raised the possibility of designing effective ways for treatment of chronic hepatitis B. In PCT WO 95/11307 (Nucleotide vector, composition containing such vector and vaccine for immunization against hepatitis) and PCT WO 95/20660 (Immunization by inoculation of DNA transcription unit) etc., different composition and routes of nucleic acid immunization have been employed; however, preparation of antigen-antibody-recombinant DNA complex vaccine and its immunogenicity has not been mentioned in such literature.

Enhanced immune responses were shown by immunization using microbial antigen complexed to specific antibodies, as reported in Venezuelan Equine Encephalomyelitis Virus (Houston W E et al. *J Inf Dis* 1977;155:600), tetanus toxoid (Stoner R D et al. *J Immunol* 1963;91:761), hepatitis B surface antigen (Chang T S. *Immunology Today* 1985;6:245). In addition, mice immunized with solid-matrix-antibody-antigen complexes of multivalent antigens (Herpes simplex virus glycoprotein D, influenza virus HA protein, simian virus HN proteins etc.) showed vigorous humoral and cellular immune responses (Randall R E et al. *J Virol* 1989;63:1808). Such published manuscripts have described only the use of polyclonal or monoclonal animal antibodies complexed to antigens to induce immune responses. Immune responses were improved, but there was no description of using the complex for treatment of chronic persistent infections. One of the present inventors patented (in China) and published in the literature using hepatitis B vaccine complexed to human specific immunoglobulins against Hepatitis B vaccine (HBIG) to treat chronic hepatitis B patients (Wen Y M et al. *Lancet* 1995;345:8964). To date, no antigen-antibody complex including incorporation of recombinant plasmid DNA as a complex vaccine has been described.

SUMMARY OF THE INVENTION

This invention provides a vaccine and/or immunogenic composition composed of antigen(s) of microbial source, its(their) specific antibody(s) and recombinant plasmid DNA(s) from the gene or genes of microbes or other sources as immunogen or adjuvant. Immunization with this complex vaccine can significantly enhance host humoral and cellular immune responses, and thus can be used to prevent or treat subjects who are immune tolerant or immune defective against specific microbial infections. This complex vaccine can be used to treat chronic persistent infected patients or asymptomatic carriers.

DETAILED DESCRIPTION

The technology of this invention is to use one or more natural or recombinant antigen(s) and its (their) specific antibody(s) and recombinant plasmid DNA containing one or more gene(s) coding for microbial proteins and other proteins to prepare a complex vaccine and/or immunogenic composition. Specifically, microbial protein antigen and its specific antibody or high titer immunoglobulin (animal or human source) were separately diluted and titrated by chessboard method, to assay for the best combination ratio of antigen-antibody complex. According to the property of the specific antigen protein used and the affinity of the antibody used, antigen and antibody were incubated at 37° C. for 2–4 hours, and spinned at 12,000 rpm to separate the precipitate. The remnant antigen and antibody in the supernatant can be very little and absorbence (A) assayed by Enzyme-linked immuno-sorbent assay (ELISA) can both be less than 0.4, in the appropriate antigen-antibody complex tube. After removal of the supernatant, the same amount of antigen as titrated in the appropriate ratio study was further added to the precipitate to ensure proper amount of antigen in excess, and subsequently, recombinant plasmid DNA (pCMV HBs) was added. This recombinant plasmid DNA contains eukaryotic cell expression element, such as pcDNAI/Amp (Invitrogen product), VR1012 (Vical product), PCI/neo (Promega product) etc. After digestion with restriction enzyme EcoRI, Hepatitis B virus surface antigen (HBsAg) encoding gene or the core gene of Hepatitis C virus is inserted to construct the recombinant plasmid DNA. In addition, recombinant plasmid DNA can be constructed with gene(s) encoding for one or more microbial protein(s), which is same as the microbial antigen used for preparation of antigen-antibody complex or is of another microbial origin. The quantity of recombinant plasmid DNA added is 20–100 times of the quantity of the antigen used. When this complex vaccine was used to immunize mice, enhanced specific humoral and cellular immune responses were induced, indicated by higher titer of specific IgG antibodies, including subclasses of IgG1, IgG2a, IgG2b; higher stimulation index in specific lymphocyte proliferation assay and higher levels of interleukin-2, interferon-γ production than those in the control groups.

As indicated above, the vaccine and/or immunogenic composition and preparation of this invention is different from all previously claimed or disclosed vaccines, and since the mechanisms of DNA immunization have not been fully clarified, the potential advantages and uses of this complex vaccine could be listed as follows:

(1). Immunogens can be presented both exogenously and endogenously. When appropriate ratio of antigen was complexed to the specific antibody to construct a more effective immunogenic complex (IC), uptake of antigen was enhanced via the Fc receptors of antigen presenting cells (APC) by the Fc fragment of antibodies. By this means, efficiency of the exogenous antigen presentation could be increased. When recombinant plasmid DNA was added to this IC, the recombinant plasmid DNA can be ingested together with the IC, and subsequently the encoded antigen protein could be expressed in the APCs and presented as an endogenous antigen. The complex vaccine described in this invention would therefore be presented both by the exogenous and the endogenous pathways, mimicking both the inactivated microbial vaccine and the attenuated vaccine, comprising a new type of vaccine.

(2). This vaccine and/or immunogenic composition can induce more potent humoral and cellular immune responses. It has been shown that IC could induce higher titer of antibodies and higher stimulation index (SI) of lymphocytes in mice than those in mice immunized with only the antigen. Since recombinant plasmid DNA immunization could induce specific cytotoxic T cells (CTL) and release higher levels of certain lymphokines, additive or synergistic effect resulting in enhanced humoral and cell mediated immune responses can be attained.

(3). More rapid immune responses could be generated. When DNA vaccine and/or immunogenic composition was used to immunize animals, according to the different types of recombinant DNA employed, DNA encoded proteins could be expressed in permissible cells and APCs are later involved to induce immune responses. Incorporation of DNA with IC can enhance the uptake of DNA into APCs and thus, expedite induction of cellular and humoral immune responses, which can be more effective than immunization only with recombinant DNA.

(4). Multivalent vaccines and/or immunogenic composition can be prepared. In some microbes (e.g. some RNA viruses), it is difficult to prepare stable and effective DNA vaccines and/or immunogenic composition or it is difficult to culture large amount of microbes for vaccine and/or immunogenic composition preparation, it will be possible to use available microbial antigen-antibody complex system and add the recombinant plasmid DNA from one or more microbes to construct multivalent effective vaccines.

(5). Less antigen or DNA is required in this vaccine and/or immunogenic composition. The combination of recombinant DNA and IC as immunogen can decrease the amount of antigen or DNA necessary to induce immune responses. The incorporation of DNA into the IC can also stabilize the DNA in host, and further decrease the necessary quantity of DNA for immunization.

(6). Increased probability of contact of antigen and DNA with immune and permissible cells. IC not only can be efficiently attached to Fc receptor on APCs, but also (due to the aggregation of antigens) would contact more cells which have receptors for the antigen. The recombinant DNA incorporated into the IC can have more chances to gain access into APCs and permissible cells for presentation and expression of the encoded antigens.

(7). Expand the routes of vaccination, immunization or administration. DNA vaccination has great potential for prevention and treatment of diseases. However, due to the degradation of naked DNA which is unpreventable in vivo and to the critical techniques necessary for effective DNA immunization, there are still obstacles for employing this vaccine in practice. In the present invention, antigen-antibody-DNA vaccine can be delivered by ordinary intramuscular injections, not necessarily critical to use specific intramuscular injection techniques, and it would not result in significant variation in the immune responses from individual recipient, which was usually observed in naked DNA immunization. Besides, since the incorporated DNA is stabilized in this complex vaccine, it could be used via respiratory tract, via vaginal or other topical routes and thus broadens the routes for vaccination of IC and DNA vaccines.

Procedures for preparation of the IC-recombinant complex vaccine and/or immunogenic composition of this invention are illustrated with immunogen from hepatitis B virus and are as follows:

1). Recombinant or plasma-derived hepatitis B surface antigen (HBsAg) was complexed to high titer antibodies against HBsAg (anti-HBs) of animal or human origin or hepatitis B specific immunoglobulin (HBIG). The concentration of HBsAg is typically selected from 0.5–5 μg/ml and the titer of hepatitis B specific antibody or specific immunoglobulin is typically selected 1:1600–1:12,800 (by ELISA) or HBIG with 200–400 IU, at the protein content of 0.5–5 μg/ml.

2) The two components were separately diluted starting from 1:50 at 5 fold dilution and titrated by chessboard method. All tubes were incubated at 37° C. for 2 hours and kept at 4° C. for 12–20 hours. After centrifugation at 12,000 rpm for 30 minutes, the supernatant from each tube was collected and assayed separately for HBsAg and anti-HBs. When the remnant HBsAg and anti-HBs assayed were at absorbency <0.4 by ELISA, this ratio was determined as the appropriate ratio tube. The same quantity of antigen used in the appropriate tube was further added to the appropriate tube precipitate for resuspension.

3) Plasmid which contains the encoding gene fragment of HBsAg, driven by the early promoter of cytomegalovirus for expression of HBsAg in eukaryotic cells, was amplified and purified by column chromatography, and highly purified recombinant plasmid DNA was collected. To the prepared HBsAg-anti-HBs complex suspension, recombinant plasmid DNA was added at the concentration of 20–100 times of the quantity of HBsAg used.

4) According to the purpose of usage of the vaccine (preventive or therapeutic), aluminum hydroxide may be added as the adjuvant, and this complex vaccine can be examined for safety, toxicity and sterility and other necessary tests to be qualified as for human use.

The present invention is described with accompanying examples. It should be understood, however, that the description following is illustrative only and should not be taken in any way as a restriction on the generality of the invention described above.

EXAMPLES

Example 1

Experimental results of humoral immune responses in groups of mice immunized with HBsAg alone, HBsAg-anti-HBs, and HBsAg-anti-HBs-recombinant DNA encoding gene fragment of HBsAg showed that anti-HBs titer was the highest in the group of mice immunized with HBsAg-anti-HBs-recombinant plasmid DNA.

To 27.5 $\mu$g of plasma-derived HBsAg, 47 $\mu$l of mouse anti-HBs (ELISA titer 1:3200) diluted to 1:30 was added to prepare antigen-antibody complex and diluted to the appropriate volume. One hundred micrograms of recombinant plasmid DNA which contains encoding gene of HBsAg and the CMV promoter was added to the antigen-antibody complex. Forty eight Balb/c mice divided into 8 groups, each consisted of 6 mice were separately injected intramuscularly with the immunogen as indicated in Table 1 and boosted again at 8 weeks after the first injection. Antibody titer was assayed by ELISA. Results showed that in the group of mice immunized with antigen-antibody-recombinant DNA, anti-HBs was detected earlier and with higher titer than the other groups. This was more significant when mice were immunized with the complex vaccine using aluminum hydroxide as the adjuvant. Mice immunized with the empty vector could not induce anti-HBs; mice immunized either only with HBsAg or anti-HBs could not induce anti-HBs or only at very low titer. Another groups of mice were immunized without using aluminum hydroxide as the adjuvant, which showed that plasmid DNA could significantly enhance antibody responses In Table 1, the percentages of anti-HBs seroconversion in the 8 groups are shown (boosted at 8 weeks). Table 2 shows the titer of anti-HBs of different groups. Table 3 shows the anti-HBs responses in mice induced without aluminum hydroxide adjuvant. Mouse sera were assayed 6 weeks after the 1st injection and 3 weeks after boosting.

TABLE 1

Percentages of anti-HBs seroconversion in mice

| Groups | Immunogen | Weeks 4 | 6 | 8 | 9 |
|---|---|---|---|---|---|
| 1 | HBsAg | 0 | / | 17 | 83 |
| 2 | anti-HBs | 0 | / | 0 | 0 |
| 3 | recombinant DNA | 67 | 67 | 83 | 80 |
| 4 | HBsAg-anti-HBs | 20 | 60 | 60 | 100 |
| 5 | HBsAg-anti-HBs-Al$(OH)_3$ | 100 | 100 | 100 | 100 |
| 6 | HBsAg-anti-HBs-DNA | 100 | 100 | 100 | 100 |
| 7 | HBsAg-anti-HBs-DNA-alum | 100 | 100 | 100 | 100 |
| 8 | vector DNA | 0 | / | 0 | 0 |

TABLE 2

Titer of anti-HBs in different groups of mice

| Groups* | 1st injection <1:400 | 1:800–1:1600 | <=1:400 | 2nd injection 1:800–1:1600 | 1:3200–1:12800 | >=1:25600 |
|---|---|---|---|---|---|---|
| 1 | 1 | 0 | 4 | 1 | 0 | 0 |
| 2 | 0 | 0 | 0 | 0 | 0 | 0 |
| 3 | 5# | 0 | 3 | 1 | 0 | 0 |
| 4 | 3 | 0 | 4 | 1 | 0 | 0 |
| 5 | 2 | 3 | 0 | 0 | 5 | 0 |
| 6 | 2 | 4 | 0 | 0 | 6 | 0 |
| 7 | 3 | 3 | 0 | 0 | 0 | 6 |
| 8 | 0 | 0 | 0 | 0 | 0 | 0 |

*Groups were immunized with immunogens same as those of Table 1
One mouse died not related to immunization

TABLE 3

Anti-HBs responses in mice immunized with antigen-antibody-recombinant plasmid DNA (without aluminum hydroxide)

| Immunogen | 1st injection anti-HBs (average ± SD) | 2nd injection anti-HBs (average ± SD) |
|---|---|---|
| HBsAg | $<10^2$ | $10^{2.3} \pm 10^{0.4}$ |
| IC(HBsAg-anti-HBs) | $10^2$ | $10^{4.7} \pm 10^{0.5}$ |
| pHBV DNA* | $10^{2.3} \pm 10^{0.1}$ | $10^{2.9} \pm 10^{0.2}$ |
| IC + pHBV DNA | $10^{2.8} \pm 10^{0.1}$ | $10^{4.9} \pm 10^{0.2}$ |
| IC + vector DNA | $10^{2.7} \pm 10^{0.3}$ | $10^{4.9} \pm 10^{0.2}$ |
| HBsAg + pHBV DNA | $10^{2.6} \pm 10^{0.4}$ | $10^{4.6} \pm 10^{0.7}$ |
| HBsAg + vector DNA | $10^{2.2} \pm 10^{0.1}$ | $10^{4.7} \pm 10^{0.3}$ |

*recombinant plasmid DNA with insert of HBV S gene

Example 2

In mice immunized with antigen-antibody-recombinant plasmid DNA, the splenic cells when stimulated with specific antigen, produced higher level of interleukin-2 than mice immunized only with recombinant plasmid DNA or only with the antigen-antibody.

Plasma-derived purified HBsAg and mouse anti-HBs (ELISA titer 1:3200) were complexed to construct immunogenic complex (IC). Recombinant plasmid DNA was added to this complex and 5 groups of Balb/c mice (6 in each group) were separately immunized with different immunogens. Group 1 was immunized with 1 $\mu$g of HBsAg; Group 2 with IC containing equivalent HBsAg of 1 $\mu$g, Group 3 with recombinant HBV DNA 200 $\mu$g; Group 4 with HBsAg-anti-HBs-recombinant DNA containing 1 $\mu$g HBsAg and 200 $\mu$g of recombinant HBV DNA; Group 5 was immunized with vector DNA as controls. After immunization, splenic cells were pooled, cultured and stimulated with HBsAg. Mouse IL-2 assay kit (Amersham product) was used to monitor the IL-2 in the cultured supernatant. Results showed that HBsAg-anti-HBs-recombinant DNA immunized mice splenic cell supernatant had the highest level of IL-2, indicating that the complex vaccine of this invention could significantly increase the specific cell mediated immune responses in hosts.

Table 4 shows the interleukin-2 levels of splenic cells from different groups of mice stimulated with HBsAg.

nized with HCV-c-DNA alone or in the complex vaccine. This study indicates that recombinant plasmid DNA harboring microbial gene fragment which is different from that of the antigen protein used could enhance the antibody responses induced by the protein antigen. At the same time, antibody induced by immunization only with the recombinant plasmid DNA was similar to that induced using recombinant plasmid DNA complexed to antigen-antibody.

Table 5 shows the anti-HBs detected in sera from different groups of mice, while Table 6 shows the titer and the absorbency of antibody against HCV core protein.

TABLE 5

Anti-HBs (titer and Absorbence) in different groups of mice

| | mouse # | | | | | | | | | | | |
|---|---|---|---|---|---|---|---|---|---|---|---|---|
| | First Injection | | | | | | Second Injection | | | | | |
| Immunogen | 1 | 2 | 3 | 4 | 5 | 6 | 1 | 2 | 3 | 4 | 5 | 6 |
| HBsAg-anti-HBs | | | | | | | | | | | | |
| (IC) | | | | | | | | | | | | |
| serum $10^{-2}$ | 0.43 | 0.51 | 0.86 | 0.71 | 0.54 | 0.50 | | | | | | |
| serum $10^{-4}$ | | | | | | | 1.52 | 0.59 | 1.19 | 0.84 | 1.52 | 1.84 |
| serum $10^{-5}$ | | | | | | | 0.22 | 0.14 | 0.28 | 0.18 | 0.30 | 0.37 |
| HCV-c-DNA | | | | | | | | | | | | |
| serum $10^{-2}$ | 0.06 | 0.07 | 0.07 | 0.08 | 0.05 | 0.06 | 0.06 | 0.06 | 0.05 | 0.06 | 0.06 | 0.07 |
| IC + HCV c DNA | | | | | | | | | | | | |
| serum $10^{-2}$ | 1.31 | 1.81 | 0.92 | 1.63 | 0.66 | 1.23 | | | | | | |
| serum $10^{-3}$ | 0.23 | 0.20 | 0.16 | 0.31 | 0.13 | 0.23 | | | | | | |
| serum $10^{-4}$ | | | | | | | 1.85 | >2.5 | 1.80 | 1.44 | 1.99 | >2.5 |
| serum $10^{-5}$ | | | | | | | 0.46 | 0.69 | 0.40 | 0.39 | 0.41 | 0.55 |

TABLE 4

Interleukin-2 from splenic cells stimulated with HBsAg

| Groups of mice immunized | IL-2 pg/ml |
|---|---|
| 1. HBsAg | 111 |
| 2. HBsAg-anti-HBs | 122 |
| 3. Recombinant plasmid DNA (pHBV DNA) | 254 |
| 4. HBsAg-anti-HBs-pHBV DNA | 307 |
| 5. Vector DNA (control) | 119 |

Example 3

To study the immunization of antigen-antibody complex and plasmid DNA from different sources, mice were separately immunized with HBsAg-anti-HBs, recombinant plasmid DNA harboring the core gene fragment of hepatitis C (HCV-c-DNA), and complex vaccine constructed of both components. Serum samples were studied 4 weeks after first immunization and 2–6 weeks after boosting (8 weeks after the first immunization), assayed for anti-HBs (ELISA) as well as for antibodies against hepatitis C virus core protein. For assay of HCV core antibody, recombinant HCV core expressed as HCV core and GST fusion protein was used to coat wells of Immunolon II plates. Peroxidase labeled rabbit anti-mouse IgG was used as the second antibody in the ELISA. Results showed that anti-HBs was higher in mice immunized with HBsAg-anti-HBs-HCV-cDNA than that in mice which were immunized without plasmid DNA. The titer of anti-HCV core antibody was similar in mice immu-

TABLE 6

Antibody against HCV core protein (titer and Absorbence)

| | 6 weeks after being boosted mouse # | | | | | |
|---|---|---|---|---|---|---|
| Immunogen | 1 | 2 | 3 | 4 | 5 | 6 |
| HBsAg-anti-HBs (IC) serum 1:20 | <0.1 | <0.1 | <0.1 | <0.1 | <0.1 | <0.1 |
| HCV-cDNA serum 1:20 | 0.24 | 0.23 | D* | 0.45 | 0.38 | 0.48 |
| IC + HCV-cDNA serum 1:20 | 0.33 | 0.27 | 0.42 | 0.25 | 0.42 | 0.38 |

D* died
positive control 0.33;
negative control 0.045

What is claimed is:

1. A composition comprising the hepatitis B surface antigen, an antibody against the hepatitis B surface antigen, and a recombinant plasmid DNA encoding the hepatitis B surface antigen or encoding the full-length hepatitis C core gene.

2. The composition according to claim 1, wherein the recombinant plasmid DNA encoding the hepatitis B surface antigen encodes the full-length hepatitis B surface antigen.

3. The composition according to claim 1, wherein the hepatitis B surface antigen comprises the full-length hepatitis B surface antigen.

4. The composition according to claim 1, comprising an antigen of natural or recombinant origin.

5. The composition according to claim 1, wherein the antibody is recombinant or is prepared by immunization of non-human animals.

6. The composition according to claim 1, wherein the recombinant DNA comprises a CMV promoter.

7. A method for preparing a composition, the composition comprising the hepatitis B surface antigen, an antibody against the hepatitis B surface antigen, and a recombinant plasmid DNA encoding the hepatitis B surface antigen or encoding the hepatitis C core gene;

the method comprising:

preparing a complex of the hepatitis B surface antigen and the antibody;

adding to the complex the recombinant plasmid DNA encoding the hepatitis B surface antigen or encoding the hepatitis C core gene at the ratio of 20–100 μg DNA to 1 μg of antigen to yield the composition.

8. The method according to claim 7, wherein preparing comprises:

diluting the hepatitis B surface antigen, diluting the antibody separately from the hepatitis B surface antigen, titrating and co-incubating the antibody using a chess-board method;

centrifuging the incubation tubes containing the antigen and antibody separately;

ELISA testing the supernatants for content of antigen or antibody separately;

selecting a pair of antigen tube and an antibody tube, the supernatants of which both show absorbance by ELISA of less than 0.4;

preparing a mixture of the antigen and antibody in ratio indicated by the pair of tubes.

9. The method according to claim 8, wherein co-incubating comprises incubating at 37° C. for 0.5–2 hours followed by standing at 4° C. for 12–20 hours.

10. The method according to claim 7, wherein the antigen concentration is 0.5–5 μg/ml, and the antibody titer is 1:1600–12,800 by ELISA.

11. The method according to claim 7, wherein the recombinant plasmid DNA further comprises a CMV promoter.

* * * * *